US00PP33653P2

(12) United States Plant Patent
Meilland

(10) Patent No.: US PP33,653 P2
(45) Date of Patent: Nov. 23, 2021

(54) BEDDING ROSE PLANT NAMED 'MEIZILENA'

(50) Latin Name: *Rosa hybrida*
Varietal Denomination: MEIZILENA

(71) Applicant: THE CONARD PYLE COMPANY, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/128,518

(22) Filed: Dec. 21, 2020

(30) Foreign Application Priority Data

Sep. 24, 2020 (QZ) ..... PBR 2020/2338

(51) Int. Cl.
*A01H 5/02* (2018.01)
*A01H 6/74* (2018.01)

(52) U.S. Cl.
USPC ..... Plt./151
CPC ..... *A01H 6/749* (2018.05)

(58) Field of Classification Search
USPC ..... Plt./151
CPC ..... A01H 6/749; A01H 5/02
See application file for complete search history.

(56) References Cited

U.S. PATENT DOCUMENTS

PP18,102 P2 10/2007 Lim
PP27,894 P3 4/2017 Meilland

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEIZILENA', is disclosed. The new variety forms on a nearly continuous basis attractive, cup shaped, red colored flowers. The red coloration of the flower intensifies gradually with the opening of the flower. Attractive, dense and glossy foliage is formed, which contrasts beautifully with the blossoms. An erected growth habit is displayed. The new variety is well suited for providing attractive ornamentation in the landscape.

1 Drawing Sheet

Botanical/commercial classification:
Latin name—*Rosa hybrida.*
Varietal denomination—'MEIZILENA'.

CROSS-REFERENCE TO RELATED APPLICATIONS

This application claims priority to Plant Breeders' Right Application Number 2020/2338, which was filed at Community Plant Variety Office in the European Union on Sep. 24, 2020, the contents of which are hereby incorporated by reference for all purposes.

SUMMARY OF THE INVENTION

The new variety of *Rosa hybrida* plant was created by artificial pollination in Le Cannet des Maures, Var, France, wherein two parents were crossed which previously had been studied in the hope that they would contribute the desired characteristics. The female parent (i.e., the seed parent) was the 'ADHARMAN' variety (non-patented). The male parent (i.e., the pollen parent) was the 'BAICENT' variety (U.S. Plant Pat. No. 18,102).

The parentage of the new variety can be summarized as follows:

'ADHARMAN' x 'BAICENT'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms a red colored flower, wherein the red coloration of the flower intensifies gradually with the opening of the flower, and (b) exhibits a dense and glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'ADHARMAN' variety (i.e., the seed parent) displays smaller flowers compared to the new variety. The 'BAICENT' variety (i.e., the pollen parent) displays yellow colored flowers, whereas the new variety displays red colored flowers. Moreover, the new variety can be readily distinguished from other similar non-parental varieties. For example, the 'MEIANYCID' variety (U.S. Plant Pat. No. 27,894) displays yellow colored flowers, whereas the new variety displays red colored flowers.

The new variety has been found to undergo asexual propagation in Le Cannet des Maures, Var, France by a number of routes, including softwood cuttings and grafting t-bud. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIZILENA'.

The first offer for sale of the new variety was Oct. 23, 2020 in the United States of America by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one years of age and were observed during July while budded on Rosa Laxa and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—observe.

Element 8—illustrates a specimen of a fully open flower—plan view—reverse.

Element 9—illustrates a specimen of a fully open flower—plan view—observe.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 3 leaflets—plan view—under surface.

Element 16—illustrates a specimen of a leaf with 5 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of one-year-old specimens of the new variety during July while budded on Rosa Laxa and growing outdoors at Le Cannet des Maures, Var, France.

Commercial classification: Bedding Rose Plant.

Plant:

*Habit*.—Erected.

*Height*.—Approximately 120 cm on average.

*Width*.—Approximately 100 cm on average.

Branches:

*Color*.—Young stems: commonly near Yellow-Green Group 146C. Adult wood: commonly near Green Group 143A.

*Length of main stem*.—Typically 30 to 80 cm on average.

*Young shoots*.—Anthocyanin coloration: strong intensity and commonly near Greyed-Purple Group 183A.

*Thorns*.—Configuration on adult stems: slightly concave and elongated on the upper surface and concave on the under surface. Long prickles — quantity: commonly approximately 3 thorns per 10 cm long young stem and commonly 7 thorns per 10 cm long adult stem. Long prickles — base shape: oval and rather short. Long prickles — size: typically 0.7 to 0.8 cm in length on average on young stems and adult stems. Long prickles — color: commonly near Yellow-Green Group 146C suffused with near Greyed-Orange Group 176C on young stems and commonly near Greyed-Orange Group 177B on adult stems. Small prickles — quantity: commonly approximately 22 thorns per 10 cm long young stem and commonly 10 thorns per 10 cm long adult stem. Small prickles — base shape: short and oval. Small prickles — size: typically 0.1 to 0.5 cm in length on average on young stems and adult stems. Small prickles — color: commonly near Yellow-Green Group 146C suffused with near Greyed-Orange Group 176C on young stems and commonly near Greyed-Orange Group 177B on adult stems.

Foliage:

*General appearance*.—Dense with a glossy aspect.

*Number of leaflets*.—3 and 5; most often 5.

*Terminal leaflet*.—Length: typically 3.5 to 5.5 cm on average. Width: typically 2.5 to 4.5 cm on average.

*New foliage*.—Upper surface color: commonly near Yellow-Green Group 146A suffused with an anthocyanin coloration of near Greyed-Purple Group 183A. Under surface color: commonly near Yellow-Green Group 146C strongly suffused with anthocyanin coloration near Greyed-Purple Group 183A.

*Adult foliage*.—Upper surface color: commonly near Yellow-Green Group 147A. Under surface color: commonly near Yellow-Green Group 147B. Anthocyanin coloration: absent.

Leaflets:

*Shape*.—Tip: acuminate. Base: rounded.

*Glossiness of upper surface*.—Strong to very strong.

*Texture*.—Leathery.

*General appearance*.—Oval.

*Edge*.—Slightly denticulate.

*Serration*.—Small and single.

*Undulation on the margin*.—Very weak.

*Petiole rachis*.—Color of upper surface: commonly near Green Group 137A. Color of under surface: commonly near Green Group 137A.

*Petioles*.—Upper surface: no glandular. Under surface: few prickles. Color of upper surface: commonly near Yellow-Green Group 146B. Color of under surface: commonly near Yellow-Green Group 146A. Petiole length of terminal leaflet: typically 1.5 to 2.5 cm on average.

*Stipules*.—General appearance: adnate, pectinate and narrow. Length: typically 1.1 to 1.3 cm on average. Width: typically 0.1 to 0.2 cm on average. Color of upper surface: commonly near Yellow-Green Group 146A. Color of under surface: commonly near Yellow-Green Group 146B.

Inflorescence:

*Number of flowers per stem*.—Typically 1 to 5 flowers per stem.

*Lastingness of the bloom*.—On the plant: approximately 10 to 12 days on average.

*Bud*.—Shape: conical. Size: medium. Length: approximately 3.0 cm on average. Width: approximately 1.5 cm on average. Color as calyx breaks: upper surface: commonly near Red Group 46A suffused with near Yellow-Orange Group 17B. under surface: commonly near Red Group 46A.

*Sepals*.—Length: typically 3.0 to 3.5 cm on average. Width: typically 0.5 to 1.0 cm on average. Shape: at the top: elongated and narrow, at the base: upright. Extensions: commonly typically 0 to 4 present, length is approximately 0.5 cm on average, width is near 0.1 cm on average. Upper surface: texture: tomentous. color: commonly near Green Group 143D. Under surface: texture: smooth. color: commonly near Green Group 143C.

*Receptacle*.—Color: commonly near Green Group 143A. Length: approximately 0.8 cm on average. Width: approximately 0.7 cm on average. Surface: smooth. Shape: funnel shaped.

*Peduncle*.—Length: typically 2.5 to 5.0 cm on average. Width: approximately 0.3 cm on average. Surface: glandular. Color: commonly near Yellow-Green Group 144A.

*Flower*.—Average diameter when fully open: typically 7.0 to 8.0 cm on average. Shape: cup shaped. Type: double. Number of petals under normal conditions: typically 20 to 25 petals on average. Shape of the petal: base: pointed. Top: rounded slightly cordiform. Texture of the petal: leathery. Petal length: typically 2.5 to 3.5 cm on average. Petal width: typically 2.5 to 3.5 cm on average. Petal arrangement: imbricated without petaloids. Petal drop: petals drop off cleanly before drying. Fragrance: none. Color when opening: spot at the base: upper surface is commonly near Yellow-Orange Group 17B and under surface is commonly near Yellow-Orange Group 17C. Upper surface of the flower: commonly near Red Group 46A. Under surface of the flower: commonly near Red Group 45C. Color of the open flower: spot at the base: upper surface is commonly near Yellow-Orange Group 17B and under surface is commonly near Yellow-Orange Group 17C. Upper surface of the flower: commonly near Red Group 53C. Under surface of the flower: commonly near Red Group 55A. Anthers: number is approximately 100 on average, length is approximately 0.3 cm on average, coloration is commonly near Orange Group 26A, and arrangement is regular around styles. Filaments: length is typically 0.4 to 1.0 cm on average and coloration is commonly near Orange-Red Group 34B. Styles: length is typically 0.1 to 0.5 cm on average, coloration is commonly near Red Group 46C, and number is approximately 40 on average. Stigmas: size is approximately 0.1 cm on average and coloration is commonly near Yellow-Orange Group 22B. Pollen: not available at this stage. Hips: not available at this stage.

Development:

*Vegetation*.—Very strong.

*Blooming*.—Early in the season, very abundant and nearly continuous, typical from May to November in France.

*USDA hardiness zone*.—Zone 5.

*Tolerance to disease*.—Very good, and particularly against black spot (*Diplocarpon rosae*) and rust (Phragmidium sp.).

The new 'MEIZILENA' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIZILENA' characterized by the following combination of characteristics:

(a) forms a red colored flower, wherein the red coloration of the flower intensifies gradually with the opening of the flower, and (b) exhibits a dense and glossy foliage;

substantially as herein shown and described.

* * * * *

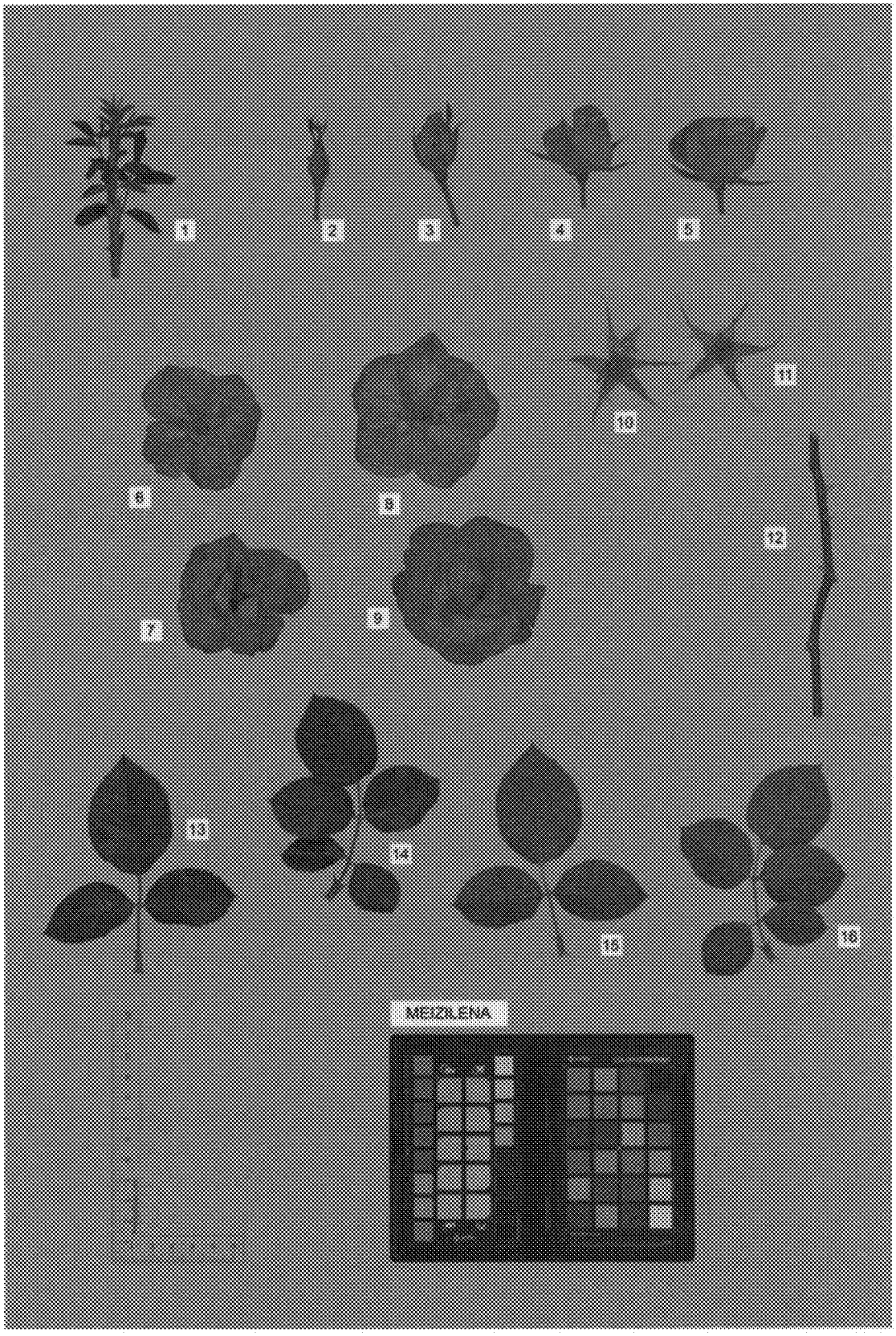
MEZILENA